United States Patent [19]

Petro et al.

[11] 4,303,740
[45] Dec. 1, 1981

[54] PROCESS FOR THE PREPARATION OF HIGHLY ACCURATE AND STABLE ELECTRODE CONTAINING A SILVER SALT

[75] Inventors: József Petró; Ernó Pungor; Klára Tóth; Ferenc Rakiás, all of Budapest, Hungary

[73] Assignee: Magyar Tudományos Akadémia, Budapest, Hungary

[21] Appl. No.: 89,880

[22] Filed: Oct. 31, 1979

Related U.S. Application Data

[63] Continuation-in-part of Ser. No. 22,414, Mar. 21, 1979.

[30] Foreign Application Priority Data

Mar. 31, 1978 [HU] Hungary .............................. MA 2971

[51] Int. Cl.$^3$ ............................................. G01N 27/26
[52] U.S. Cl. ................................ 428/548; 204/195 F; 204/195 M; 427/123; 204/290 R
[58] Field of Search .................... 428/548; 204/195 F, 204/195 M

[56] References Cited

U.S. PATENT DOCUMENTS

| | | | |
|---|---|---|---|
| 3,354,069 | 11/1967 | Jerrold-Jones et al. | 204/195 F |
| 3,446,726 | 5/1969 | Pungor et al. | 204/195 M |
| 3,607,710 | 9/1971 | Farren et al. | 204/195 M |
| 3,662,745 | 5/1972 | Cosentino | 204/195 F |
| 3,856,649 | 12/1974 | Genshaw et al. | 204/195 F |

*Primary Examiner*—Brooks H. Hunt
*Attorney, Agent, or Firm*—Gabriel P. Katona

[57] ABSTRACT

The invention relates to a new process for the preparation of highly accurate and stable silver-silver salt reference electrode. According to the invention a homogeneous mixture is formed from silver powder and a powdered silver salt, then a paste is prepared by blending the mixture with a liquid binding agent capable of adhering to metals, applying the paste onto the surface of an electrode base, allowing the paste to harden and then subjecting the electrode to a heat treatment between 100° C. and 250° C. In this latter step a porous silver-silver salt layer is formed on the metal base, which renders the electrode highly accurate and stable.

Ion selective measuring electrodes are prepared essentially in the same manner with the difference that silver is replaced partly or entirely by graphit.

14 Claims, No Drawings

PROCESS FOR THE PREPARATION OF HIGHLY ACCURATE AND STABLE ELECTRODE CONTAINING A SILVER SALT

This application is a continuation-in-part of Ser. No. 22,414 filed Mar. 21, 1979.

The invention relates to a novel process for the preparation of a highly accurate and stable electrode containing a silver salt. The invention relates further to an electrode containing a silver salt whenever prepared by this new process.

More particularly the invention relates to a new process for the preparation of silver-silver salt reference electrodes having a high accuracy and stability. The process of the invention is especially suitable to the preparation of silver-silver halide and silver-silver sulfide reference electrodes.

The invention also comprises a new process for the preparation of ion selective measuring electrodes containing at least one of silver and graphite in combination with a silver halide or silver sulfide.

Among the silver halides the chloride, bromide and iodide are preferable in both cases.

As known, silver-silver chloride electrode is prepared electrochemically in a way that a silver chloride layer is formed on metallic silver by electrolysis in a hydrochloric acid solution. The adherence of silver chloride layer to the metal surface is, however, rather poor. Moreover, the silver chloride precipitate is ageing upon storage with a simultaneous change in its grain size distribution. Owing to these phenomena the accuracy of the electrode decreases and its stability is insufficient. A further disadvantage of the electrode prepared as described above is that its potential does not set in immediately. It is also disadvantageous that these electrodes should be stored under specific conditions, i.e. in solutions containing chloride ions, in order to restore their properties (D. Ivens and J. Janz, Reference Electrodes Theory and Practice, Academic Press, New York, N.Y. USA, 1969).

According to another known method discussed in the above reference, silver-silver chloride electrode is manufactured by preparing an aqueous paste from a mixture of silver and silver chloride, applying the paste to the electrode base material, drying the layer and then igniting the product in a furnace at a temperature above 600° C. Electrodes prepared in this way show essentially the same disadvantages as given above. These electrodes, again, do not possess sufficient accuracy and stability.

A method for preparing metal-metal salt electrodes is described by Cosentino in the U.S. Pat. No. 3,662,745. Metal-metal salt electrodes are prepared by mixing a metal and a metal salt in powdered form and incorporating the mixture into a matrix capable of forming a liquid or paste, and the thus prepared liquid or paste is applied to an electrically conducting support. Then the electrode is baked at about 93° C. or air-dried to make the matrixed mixture cured. Electrodes of good conductivity and sufficient stability can be produced by this method.

Now we have found that the stability and the accuracy of the electrode can be enhanced substantially if the electrodes mentioned above are subjected to heat treatment at a temperature between 100° C. and 250° C. after the hardening of the binding agent.

On the basis of the above recognition silver-silver salt reference electrodes are prepared by admixing silver powder and a silver salt powder with a binding agent, applying the resulting mass to a metal base, and subjecting the product to heat treatment between 100° C. and 250° C. after the solidification of the binding agent. The resulting electrode contains silver and a silver salt in a very porous layer with great inner contact surface well adhering to the metal base.

Ion selective measuring electrodes are prepared in the same manner with the difference that silver can be replaced partly or entirely by graphite.

The new process for the preparation of highly accurate and stable silver-silver salt electrodes comprises the steps of (a) admixing silver powder and a powdered silver salt prepared chemically, in a weight ratio of 0.05:0.95 to 0.95:0.05 and homogenizing the mixture, (b) preparing a paste of good lubricity from the powder mixture by admixing it with a liquid binding agent capable of adhering to metals, (c) applying the paste onto an electrode base, and (d) subjecting the electrode to heat treatment between 100° C. and 250° C. after the hardening of the paste.

According to an other feature of the invention ion selective measuring electrodes are prepared by (a) admixing at least one of silver and graphite with a silver salt, both in powdered form, in a weight ratio of 0.05:0.95 to 0.95:0.05 and homogenizing the mixture, (b) preparing a paste of good lubricity from the powdered mixture by blending it with a liquid binding agent capable of adhering to metals, (c) applying the paste onto an electrode base, and (d) subjecting the electrode to heat treatment between 100° C. and 250° C. after the hardening of the paste.

The silver salt is preferably a halide such as chloride, bromide or iodide but silver sulfide can be used as well.

As mentioned above, the silver, graphite or both and the silver salt are admixed in a weight ratio of 0.05:0.95 to 0.95:0.05. Mixtures containing 2 parts by weight of silver, graphite or mixture of them along with one part by weight of silver salt, as well as those containing 2 parts by weight of silver salt along with one part by weight of silver, graphite or mixture of them proved to be preferable. The most preferred mixture contains the said two components in a weight ratio of 1:1. With respect to the quality of the resulting product it is essential that the two components are perfectly blended with each other.

Any liquid binding agent capable of adhering to metals can be used as binding agent in accordance with the invention. Two-component liquid resins are preferred, of which epoxy resins are particularly advantageous. The binding agent is applied in an amount sufficient to form a paste easily applicable to metal surfaces when admixed with the silver-silver chloride powder mixture.

Thereafter the paste formed with the binding agent is applied onto the electrode base. Silver as base metal is applied preferably in an appropriate shape, such as foil, wire or net, and the paste is allowed to harden. In the next step the electrode is subjected to heat treatment. During this procedure the paste shrinks and the solvent present in the binding agent evaporates, thereby forming a porous silver-silver chloride layer. The temperature and duration of heat treatment depend obviously on the nature of the binding agent. Thus e.g. when an epoxy resin is applied as binding agent, heat treatment is performed at about 180° to 250° C. Coatings containing a polyurethane resin as binding agent are heat treated generally at about 150° to 250° C., whereas those prepared with a polyamide acid are heated generally to 100° to 250° C. The time of heat treatment ranges from 10 minutes to 2 hours and it is preferably about 30 minutes.

In case of preparing electrodes containing silver sulfide, the heat treatment is preferably performed in a reductive atmosphere such as in hydrogen gas. Silver sulfide can thus be protected from the eventual oxidation.

Although the connection between the heat treatment and the remarkable increase of stability and accuracy of the electrodes cannot be interpreted exactly, it is believed that the binding agent prevent in the electrode material decomposes on heating while volatile substances escape from the resin. So the resin shrinks and a spongy layer is formed that has a high specific surface and a high solidity. This layer adheres well to the electrode base. Temperatures below 100° C. are insufficient for causing the formation of such a spongy layer, while a heat treatment at about 300° to 350° C. can bring about the formation of tars from the binding material and cessation of the spongy structure. Owing to the presence of tars the electrodes can become hydrophobic.

It is assumed further that the diversity of grain size of the components of the electrode cover layer decreases when the electrode is heat treated in the said temperature range. This phenomenon can result in the increase of the accuracy of the electrode.

In order to increase the porosity of the electrode cover layer, 0.1 to 1 part by weight, calculated for the weight of the powder mixture, of an organic or mineral substance capable of releasing gaseous products upon heating may be added to the powder mixture. As porosity-increasing substance preferably an ammonium salt, such as ammonium carbonate or ammonium chloride, furthermore oxalic acid, ammonium oxalate or ascorbic acid can be applied.

The electrode prepared according to the invention is conditioned for 20 to 24 hours prior to use. Accordingly, the electrode is soaked e.g. in a 0.1 molar potassium chloride solution e.g. for 20 hours. The electrode conditioned in this way can be utilized directly without any further pretreatment. Electrodes out of use for a prolonged period can also be stored in dry state, however, they should be conditioned again prior to the next utilization.

It is a further advantage of the method of the invention that it can be performed easily without applying specific apparatuses.

The process of the invention is elucidated in detail by the aid of the following non-limiting Examples.

EXAMPLE 1

One part by weight of pure silver powder is admixed with one part by weight of powdered silver chloride and 0.3 parts by weight of ammonium carbonate, both prepared from analytically pure reagents. The powder mixture is homogenized thoroughly, and then admixed with an amount of liquid epoxy resin sufficient to yield a paste of good lubricity. About 0.5 to 1 part by weight of epoxy resin is used for 1 part by weight of the silver-silver chloride powder mixture. The powder and the binding agent are blended thoroughly to form a homogeneous paste.

The homogeneous paste is applied to a silver wire, also playing the role of electric connection. After the hardening of the resin, well adhering to the metal, a compact layer firmly held on the metal surface is formed. The coated silver wire is then heated at about 200° C. for 0.5 hours. In this treatment the resin starts to decompose, solvent vapours leave the coating, and the resin shrinks, whereupon the complete layer becomes porous.

The accuracy of the resulting electrode is better than 0.01 mV.

EXAMPLE 2

One part by weight of silver powder is blended with one part by weight of silver chloride powder and 0.5 parts by weight of ammonium chloride, and the resulting homogeneous mixture is converted into a paste as given in Example 1. This paste is applied to a silver plate. After the hardening of the binding agent the electrode is subjected to heat treatment as given in Example 1.

EXAMPLE 3

One proceeds as described in Example 1 with the difference that a 15% N-methyl-pyrrolidone solution of polyamide acid is applied as binding agent.

EXAMPLE 4

One proceeds as described in Example 1 with the difference that ammonium carbonate is replaced by the same amount of ammonium chloride.

EXAMPLE 5

0.1 parts by weight of silver powder are admixed with one part by weight of silver chloride powder and 0.3 parts by weight of ammonium carbonate. The mixture is homogenized thoroughly, thereafter epoxy resin is added in an amount required to form a paste, and the components are blended thoroughly. The resulting paste is applied to a silver net, the binding agent is allowed to harden, and then the electrode is subjected to heat treatment essentially as given in Example 1.

EXAMPLE 6

A homogeneous mixture is prepared from one part by weight of silver powder, 0.1 parts by weight of silver chloride powder and 0.5 parts by weight of ammonium carbonate. The mixture is processed as indicated in Example 5.

EXAMPLE 7

1 g of silver bromide is mixed with 0.5 g of silver powder having a high specific surface and 0.5 g of ammonium carbonate is added to the mixture. The mixture is homogenized thoroughly. 1.2 g of the mixture are blended with 1.5 g of two-component liquid epoxy resin and the thus prepared paste is applied to a silver strand to form a thin layer. The process is continued as described in Example 1.

An ion selective bromide electrode is obtained the accuracy of which is the following (calculated on a level of significance of 95%):

$$E_1 = -(53.00 \pm 0.58) \log a_{Br^-} + (187.0 \pm 2.12)$$

$$E_2 = -(53.00 \pm 0.58) \log a_{Br^-} + (189.0 \pm 2.12)$$

$$E_3 = -(53.00 \pm 0.58) \log a_{Br^-} + (189.7 \pm 2.12)$$

$$E_4 = -(56.00 \pm 0.55) \log a_{Br^-} + (191.5 \pm 1.94)$$

The value of stability is lower than 0.1 mV/8 hours.

EXAMPLE 8

The process of Example 7 is repeated with the difference that 0.25 g of graphite are used instead of silver powder.

EXAMPLE 9

The process of Example 7 is repeated with the difference that a mixture of 0.3 g of silver powder and 0.2 g of graphite is used instead of silver powder.

EXAMPLE 10

1 g of silver iodide is mixed with 0.2 g of graphite, 0.5 g of ammonium carbonate and 0.25 g of ascorbic acid and the mixture is homogenized thoroughly.

1.1 g of the mixture are blended with 1.5 g of liquid epoxy resin and formed into a paste. The process is continued as described in Example 1.

An ion selective iodide electrode is obtained in this manner. The accuracy of this electrode calculated on a level of significance of 95% is as follows:

$E_1 = -(47.67\pm0.56) \log a_I - +(416.17\pm0.56)$ $E_2 = -(50.73\pm0.56) \log a_I - +(430.73\pm2.07)$ $E_3 = -(50.10\pm0.56) \log a_I - +(430.60\pm2.07)$ $E_4 = -(49.83\pm0.56) \log a_I - +(428.33\pm2.07).$ The value of stability is lower than 0.03 mV/9 hours.

EXAMPLE 11

The process of Example 10 is repeated with the difference that 0.5 g of silver powder are used instead of graphite.

EXAMPLE 12

1 g of silver sulfide is mixed with 0.25 g of graphite, 0.5 g of ammonium carbonate and 0.25 g of ascorbic acid. The mixture is homogenized. 1 g of this mixture is blended with 1.5 g of liquid epoxy resin and is formed into paste. The subsequent process steps are carried out as described in Example 1 with the difference that the heat treatment is performed in hydrogen atmosphere at a temperature of 200° C. for 30 minutes.

The accuracy of the thus obtained ion selective sulfide electrode calculated on a level of significance of 95% is as follows:

$E_1 = -(26.51\pm3.46) \log a_{S2} - -(390.51\pm11.09)$ $E_2 = -(26.04\pm3.46) \log a_{S2} - -(389.59\pm11.01).$ The value of stability is lower than 0.1 mV/6 hours.

The electrodes prepared according to the invention possess higher accuracy and higher stability than the electrodes produced by prior art processes. This fact is illustrated by the following comparative tests in which the properties of an electrode prepared according to Example 1 above are compared with the properties of electrodes prepared according to Example XIV of U.S. Pat. No. 3,662,745 referred to in the description of the prior art. These latter electrodes are referred to as electrodes A/1 and A/2 in the description of the comparative test.

The electrode is placed into a $10^{-2}$M KCl solution in a thermostate of temperature 25±0.1° C. The electrode potential (e.m.c.) is measured with a Solatron apparatus of Schlumberger A 023 type that is linked with an EMG 666 type calculator having a printer attached thereto.

According to the program of the calculator the measured data are taken continuously (at least 10 data within 1 sec.) and averaged in 5 minutes periods and the result is indicated on the printer. This program is completed with an error minimising evaluation program according to which the deviations exceeding 0.2 mV are separated and omitted unless a tendency arises to direction of the deviation.

In an other test the electrode potential is measured in a series of at least 4 solutions having different concentrations. The measuring is repeated at least three times at each concentration. The test data are indicated on a diagram the ordinate of which is the measure of the electrode potential (e.m.c.) and the abscissa is the logarithm of the ion activity in the solution. The intersection of the line determined by the data on the diagram and the ordinate corresponds to the normal potential ($E_o$) while the slope of the line (S) corresponds to the factor of the logarithmic member in the following well known equation:

$E = E_o + (RT/nF) \cdot \ln a$ wherein a is the ion activity. This equation can be expressed in the following simplified form as well:

$E = E_o + S \cdot \log a.$

The standard deviation of $E_o$ and S is the measure of the accuracy of the electrode. It is determined by statistical evaluation of the above test data in connection with the latter equation.

(a) A freshly prepared electrode A/1 is placed into a $10^{-2}$M KCl solution and the e.m.c. is measured during 4 hours and 50 minutes. The average e.m.c. value is 15.6884 mV. The maximum deviations from the average value are +0.8384 mV and −0.4463 mV, respectively.

The electrode is then conditioned in a $10^{-2}$M KCl solution for 2 hours and the e.m.c. is measured during 4 hours. The average e.m.c. value is 15.0452 mV. The maximum deviations from the average value are +0.1395 mV and −0.1320 mV, respectively.

The equation relating to the electrode potential calculated on a level of significance of 95% is as follows:

$E = (5.97\pm2.47) - (11.47\pm0.67) \log a_{Cl} - (mV)$ (b) A freshly prepared electrode A/2 is conditioned for 72 hours in a $10^{-2}$M KCl solution. Then the e.m.c. is measured during 17 hours and 10 minutes. The average e.m.c. value is 17.9534 mV. The maximum deviations are +1.1531 mV and −0.3037 mV, respectively.

The equation of the electrode potential calculated on a level of significance of 95% is as follows:

$E = (5.80\pm2.07) - (11.80\pm0.58) \log a_{Cl} - (mV).$ (c) An electrode prepared by the invention is conditioned in a 0.1 M KCl solution for 20 hours. Then the e.m.c. is measured during six hours and 20 minutes. The average e.m.c. value is 63.3334 mV. The maximum deviation is ±0.0114 mV.

The equation of the electrode potential calculated on a level of significance of 95% is as follows:

$E = (70.87\pm2.10) - (42.87\pm0.57) \log a_{Cl} - (mV).$

It is to be remarked that the method described in Example XIV of the U.S. Pat. No. 3,662,745 cannot be followed strictly because a larger amount of resin is needed for making a well applicable paste. So the powder mixture was homogenized with epoxy resin in a weight ratio of 1:1 when preparing the electrodes A/1 and A/2.

It is clearly shown that the standard deviation of the $E_o$ values is much lower in the case of electrodes of the invention than in the case of the prior art electrodes A/1 and A/2.

As it is well known, the most favourable value of S (the slope of the calibration diagram) is 59 mV. This value is about 11 mV at the prior art electrodes and about 42 mV at the electrode of the invention. So this characteristic of the electrode of the invention is more advantageous than that of the electrodes A/1 and A/2.

The standard deviation of S is higher at the electrodes A/1 and A/2 than that of the electrode of the invention.

Summing up, the accuracy of the electrodes of the invention is substantially higher than the accuracy of the prior art electrodes.

On comparing the stability values it appears that the electrode of the invention is also substantially superior to the prior art electrodes since its stability is about 0.01 mV whereas the stability of the prior art electrodes is in the order of magnitude of 0.1 mV.

We claim:

1. An improved process for the preparation of silver-silver salt reference electrode comprising mixing silver and a silver salt, both in powdered form in a weight ratio of 0.05:0.95 to 0.95:0.05, homogenizing the mixture, preparing a paste of good lubricity by blending the mixture with a liquid binding agent capable of adhering to metals, applying the paste onto the surface of an electrode base and allowing the paste to harden wherein the improvement is that the electrode is subjected to a heat treatment at a temperature between 100° C. and 250° C. after the hardening the paste.

2. A process as claimed in claim 1 which comprises using epoxy resin as binding agent.

3. A process as claimed in claim 1 which comprises adding to the powder mixture an organic or mineral substance capable of releasing gaseous products on heating in an amount of 0.1 to 1 parts by weight calculated for one part by weight of the powder mixture.

4. A process as claimed in claim 3 which comprises using at least one of ammonium carbonate, ammonium chloride and ascorbic acid as a substance capable of releasing gaseous products on heating.

5. A process as claimed in claim 1 which comprises using silver chloride, bromide, iodide or sulfide as silver salt.

6. A process as claimed in claim 1 which comprises performing the heat treatment in a reductive atmosphere is case of using silver sulfide as silver salt.

7. An improved process for the preparation of ion selection measuring electrode containing a silver salt comprising mixing at least one of graphite and silver in powdered form with a powdered silver salt in a weight ratio of 0.05:0.95 to 0.95:0.05, homogenizing the mixture, preparing a paste of good lubricity by blending the mixture with a liquid binding agent capable of adhering to metals, applying the paste onto the surface of an electrode base and allowing the paste to harden wherein the improvement is that the electrode is subjected to a heat treatment at a temperature between 100° C. and 250° C. after the hardening of the paste.

8. A process as claimed in claim 7 which comprises using epoxy resin as binding agent.

9. A process as claimed in claim 7 which comprises adding to the powder mixture an organic or mineral substance capable of releasing gaseous products on heating in an amount of 0.1 to 1 parts by weight calculated for one part by weight of the powder mixture.

10. A process as claimed in claim 9 which comprises using at least one of ammonium carbonate, ammonium chloride and ascorbic acid as a substance capable of releasing gaseous products on heating.

11. A process as claimed in claim 7 which comprises using silver chloride, bromide, iodide or sulfide as silver salt.

12. A process as claimed in claim 7 which comprises performing the heat treatment in a reductive atmosphere in case of using silver sulfide as silver salt.

13. A silver-silver salt reference electrode whenever prepared by a process claimed in any of claims 1 to 6.

14. An ion selective measuring electrode containing a silver salt whenever prepared by a process claimed in any of claims 7 to 12.

* * * * *